US007372274B2

United States Patent
Ardenkjaer-Larsen et al.

(10) Patent No.: US 7,372,274 B2
(45) Date of Patent: May 13, 2008

(54) METHODS AND DEVICES CONFIGURED FOR DISSOLVING HYPERPOLARISED SOLID MATERIAL WITH A SOLVENT WITHIN A CRYOSTAT FOR NMR ANALYSES

(75) Inventors: Jan Henrik Ardenkjaer-Larsen, Malmo (SE); Oskar H. E. Axelsson, Malmo (SE); Klaes Koppel Golman, Malmo (SE); Georg Hansson, Malmo (SE); Haukur Johannesson, Lund (SE); Rolf Servin, Malmo (SE); Mikkel Thaning, Malmo (SE); Lennart Hansson, Malmo (SE)

(73) Assignee: GE Healthcare AS, Oslo (NO)

( * ) Notice: Subject to any disclaimer, the term of this patent is extended or adjusted under 35 U.S.C. 154(b) by 795 days.

(21) Appl. No.: 10/415,968

(22) PCT Filed: Nov. 2, 2001

(86) PCT No.: PCT/EP01/12736

§ 371 (c)(1),
(2), (4) Date: Aug. 29, 2003

(87) PCT Pub. No.: WO02/37132

PCT Pub. Date: May 10, 2002

(65) Prior Publication Data
US 2004/0066193 A1 Apr. 8, 2004

Related U.S. Application Data
(60) Provisional application No. 60/256,974, filed on Jan. 5, 2001.

(30) Foreign Application Priority Data
Nov. 3, 2000 (SE) .................. 0004034

(51) Int. Cl.
*G01V 3/00* (2006.01)
*A61B 5/055* (2006.01)
(52) U.S. Cl. .................. 324/321; 324/318; 324/307; 324/319; 600/410; 600/411
(58) Field of Classification Search ........... 324/307, 324/309, 318–322; 600/410, 411
See application file for complete search history.

(56) References Cited

U.S. PATENT DOCUMENTS 3,525,928 A * 8/1970 Nagao et al. ............... 324/315

(Continued)

FOREIGN PATENT DOCUMENTS

| WO | WO97/37239 | 10/1997 |
| WO | WO98/58272 | 12/1998 |
| WO | WO01/96895 | 12/2001 |

OTHER PUBLICATIONS

Merriam Webster's Collegiate Dictionary Tenth Edition definition of the term "dissolve" on p. 337.*

*Primary Examiner*—Brij Shrivastav
*Assistant Examiner*—Tiffany A. Fetzner
(74) *Attorney, Agent, or Firm*—Robert F. Chisholm

(57) ABSTRACT

The present invention relates to devices and method for dissolving solid polarised material while retaining a high level of polarisation. In an embodiment of the present invention a material is polarised in a strong magnetic field in a cryostat 2 and then brought into solution while still inside the cryostat 2.

16 Claims, 7 Drawing Sheets

U.S. PATENT DOCUMENTS

| | | | |
|---|---|---|---|
| 4,642,206 A * | 2/1987 | Honig | 264/0.5 |
| 5,258,710 A * | 11/1993 | Black et al. | 324/309 |
| 5,617,859 A | 4/1997 | Souza et al. | 128/653.2 |
| 6,125,654 A * | 10/2000 | Honig | 62/637 |
| 6,515,260 B1 * | 2/2003 | Anderson | 219/385 |
| 6,666,047 B1 * | 12/2003 | Shah et al. | 62/637 |
| 7,102,354 B2 * | 9/2006 | Ardenkjaer-Larsen et al. | 324/321 |
| 2004/0049108 A1 * | 3/2004 | Ardenkjaer-Larsen et al. | 600/412 |
| 2004/0066193 A1 * | 4/2004 | Ardenkjaer-Larsen et al. | 324/309 |
| 2005/0225328 A1 * | 10/2005 | Ardenkjaer-Larsen et al. | 324/321 |
| 2006/0192559 A1 * | 8/2006 | Ardenkjaer-Larsen et al. | 324/321 |

\* cited by examiner

METHODS AND DEVICES CONFIGURED FOR DISSOLVING HYPERPOLARISED SOLID MATERIAL WITH A SOLVENT WITHIN A CRYOSTAT FOR NMR ANALYSES

This application is a filing under 35 U.S.C. § 371 and claims priority to international application number PCT/EP01/12736 filed Nov. 2, 2001 which claims priority to U.S. Provisional application No. 60/256,974 filed Jan. 5, 2001 and to Swedish application 0004034-5 filed Nov. 3, 2000.

FIELD OF THE INVENTION

The present invention relates to devices and methods for dissolving solid polarised materials while retaining a high level of polarisation.

PRIOR ART

The present invention relates to nuclear magnetic resonance (NMR) analysis, particularly to nuclear magnetic resonance imaging (MRI) and analytical high-resolution NMR spectroscopy. MRI is a diagnostic technique that has become particularly attractive to physicians as it is non-invasive and does not involve exposing the patient under study to potentially harmful radiation such as X-rays. Analytical high resolution NMR spectroscopy is routinely used in the determination of molecular structure.

MRI and NMR spectroscopy lack sensitivity due to the normally very low polarisation of the nuclear spins of the materials used. A number of techniques exist to improve the polarisation of nuclear spins in the solid phase. These techniques are known as hyperpolarisation techniques and lead to an increase in sensitivity. However, in order to exploit the NMR signal for in vivo medical imaging the polarised material has to be brought into solution or liquid phase before being introduced into the imaging object. For in vitro analytical NMR spectroscopy, it can also often be advantageous to bring the polarised solid material into solution. A problem exists in that the polarised solid material has to be brought into solution or liquid phase and transferred into the NMR magnet with a minimal loss of polarisation. Patent application no. WO9935508 mentions a method for dissolving solid polarised material. In this method the polarised material was manually lifted out of the cryostat and within about 1 second dissolved in deuterium oxide at 40° C. while being subjected to a magnetic field of 0.4 T. This method enhanced the polarisation by a factor of up to 21 compared to other methods of producing a solution containing polarised material. However this method has the disadvantage that as the sample is moved manually it is difficult to get reproducible results. The purpose of the present invention is to provide methods and devices for improving the prior art method for producing a solution containing polarised material.

SUMMARY OF THE INVENTION

According to the present invention, at least some of the problems with the prior art are solved by means of a device having the features present in the characterising part of independent claim 1 or 12, and methods having the features mentioned in the characterising part of claim 11 or 15. In particular the present invention provides a method and means for bringing polarised solid material from a polarising unit into solution or liquid phase with a minimal loss of polarisation. Devices and methods for producing solutions of dissolved hyperpolarised materials, e.g. contrast agents or analytical samples, are described.

Further improved devices and methods have the features mentioned in the dependent claims.

In one embodiment of the present invention a sample is polarised in a first instrument and dissolved in a second dissolving instrument connected to the first instrument. In a preferred embodiment of the invention, a polarising device and a dissolving device are combined in a single instrument, so that the transport time between being polarised and dissolved is minimised and the loss of polarisation of the sample is minimised. In an especially preferred embodiment of the invention the polarising unit and the dissolving chamber is combined with a NMR spectrometer and/or NMR imager so that the time between the sample being dissolved and analysed is minimised and the loss of polarisation of the sample is minimised. According to the present invention, polarisation may be achieved by use of a polarising agent, e.g. a compound comprising paramagnetic organic free radicals. The NMR data obtained by the use of devices and methods in accordance with the present invention may be NMR imaging data and/or NMR spectroscopy data.

DETAILED DESCRIPTION OF EMBODIMENTS ILLUSTRATING THE INVENTION

Figure 1:
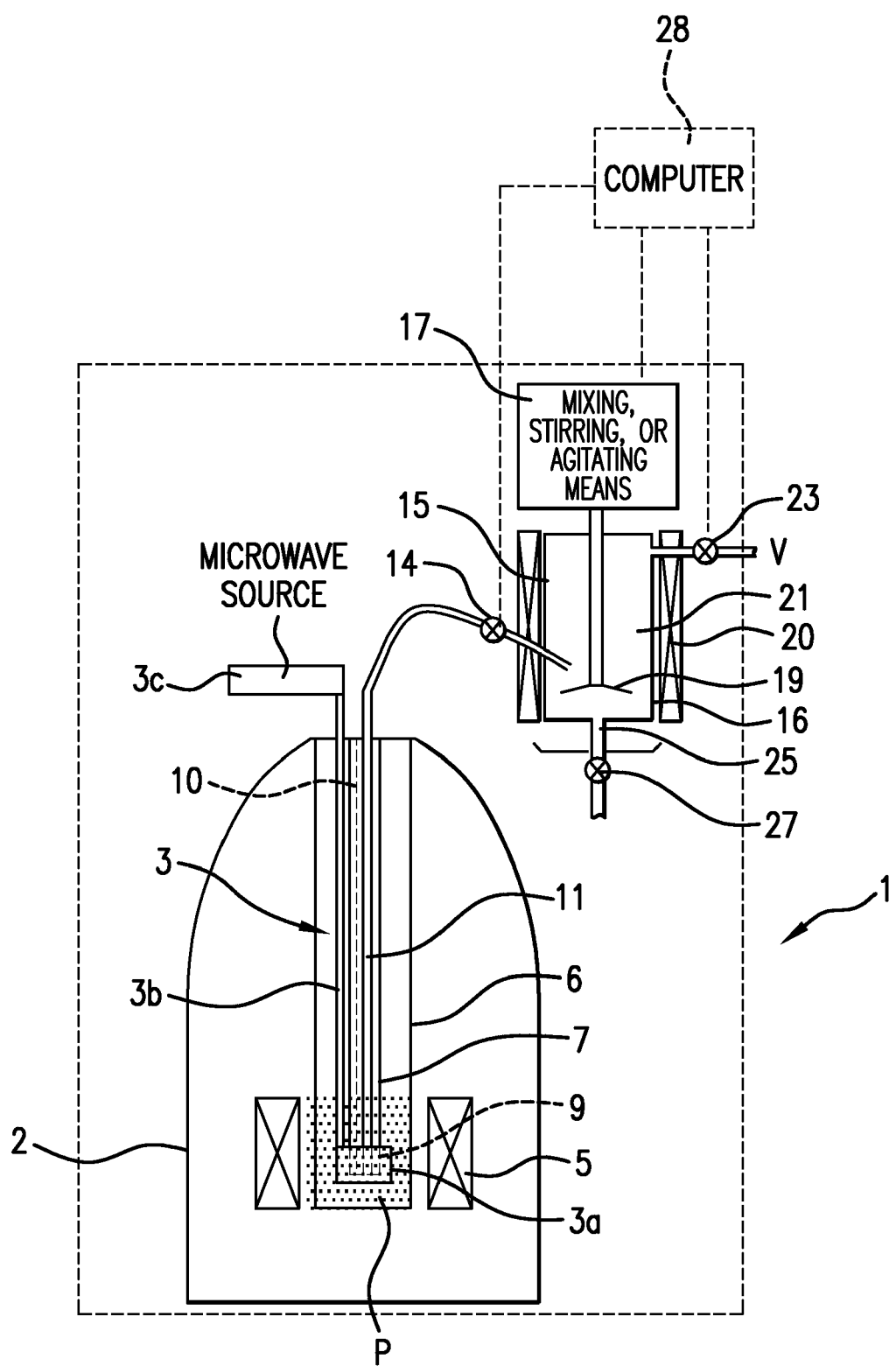
FIG. 1 shows a schematic lateral view of a first embodiment of a device in accordance with the present invention.

In methods and devices in accordance with the present invention, a solid sample of the material to be polarised can be polarised while still in the solid phase by any appropriate known method, e.g. brute force polarisation, dynamic nuclear polarisation or the spin refrigerator method, while being maintained at a low temperature (e.g. under 100 K) in a strong magnetic field (e.g. 1-25 T). After the solid material has been polarised, it is brought into solution with a minimum loss of polarisation. In the following the expression "unit for dissolved polarised material" will be considered to mean the following: a container in which solid polarised material can be brought into contact with an amount of solvent sufficient to dissolve the solid polarised material, and/or, a container in which dissolved polarised material can be stored. The expression "dissolved" means that the molecules of a substance said to be dissolved in a solvent are homogeneously distributed in said solvent.

In a first embodiment of the present invention, the dissolving occurs in a unit for dissolved polarised material that is physically separated from the polarisation device, and the unit for dissolved polarised material is also physically separated from the analysis device and therefore the polarised material needs to be transported from one device to another. In general, this has to be done rapidly, reproducibly and under special conditions, as will be described in detail below for a number of different examples.

In a second embodiment of the present invention the dissolving takes place in the same apparatus that contains the polarisation device.

In a third embodiment of the present invention the solution of polarised material is made and used while retained in a combined polarisation, dissolving and NMR analysis device.

In a fourth embodiment of the present invention, material is polarised in a polarising apparatus in close proximity to a NMR spectrometer, the polarised material is dissolved in the polarising apparatus and then quickly transferred to the analysis region of the NMR spectrometer.

The advantage of the described invention is that it provides means for bringing polarised solid material into solution with minimal loss of polarisation in a repeatable manner. This is crucial to the use of the solid state hyperpolarisation techniques in medical imaging and analytical in vitro high-resolution NMR spectroscopy. In solution, the NMR lines are narrow. This improves considerably the signal-to-noise ratio and spectral resolution, and also gives technical advantages since the sample does not have to be spun as for solid samples.

For most solid materials the relaxation rate (loss of polarisation if hyperpolarised) increases rapidly as a function of inverse field strength. Therefore, for these polarised materials it is preferable that they are kept in a strong magnetic field (e.g. greater than 0.1 T) while being handled. Other reasons for the loss of polarisation are also known, e.g. sudden changes of magnetic field orientation, strong magnetic gradients, or radio frequency fields, and these should be avoided as much as possible. The dissolving of the polarised material can be promoted by several methods. When possible, the solid material should be provided as a finely divided powder in order to allow fast dispersion and intimate contact of the solid particles and the solvent. The solid particles (or beads) and solvent can be vigorously agitated by stirring, mixing, shaking, bubbling, crushing, sonication, microwave heating, laser irradiation or any other means that will provide agitation, and optionally, heating. The temperature of the solvent can be optimised for the particular material in order to provide the fastest possible dissolving without causing unnecessary relaxation. The relaxation rate as a function of temperature and field is unique to every solid material and solvent/solute system. It is therefore also advantageous when the temperature of the solvent is optimised for minimal relaxation of the actual material being dissolved. In general, but not always, the magnetic field should be as strong as possible. This also applies to the liquid sample during the process of dissolving. The minimum $T_1$ during the process will generally increase with increasing magnetic field.

In a preferred embodiment of the present invention, a device for dissolving a solid polarised material is provided in a dynamic nuclear polarisation (DNP) system. This DNP system comprises a magnet with field strength of 0.1-25 T or more that is placed in a low loss cryostat in order to achieve optimal cryogenic hold times. For magnetic fields above ca. 2 T the magnet may be superconducting. For lower fields simpler magnets could be preferred. An especially preferred DNP system consists of a superconducting magnet designed for a field-strength of 2-25 T. The magnet is placed in an ultra low loss cryostat to achieve optimal cryogenic hold time. The field homogeneity required is sample dependent, but will typically have to be +/−0.2 mT over the sample volume. This can be achieved by providing field shims even for large samples. Correspondingly, the stability of the field during polarisation should be better than the homogeneity criterion, i.e. the field drift should be less than the inhomogeneity. The magnet is designed to accommodate a low temperature space to cool the sample. The preferred superconducting magnet cryostat is preferably provided with a pumped helium bath or at least a cold space in the bore of the magnet. The helium bath may be contained in a tube that is thermally insulated (e.g. vacuum insulated) from the magnet helium reservoir but connected to it by a capillary to allow filling from the magnet reservoir. The low temperature space may simply be a cylinder (made from thin-walled stainless steel or copper or another non-magnetic material or combinations thereof) with the lower end closed. In order to obtain the lowest possible temperatures and lowest cryogenic consumption, the low temperature space is preferably placed in vacuum inside the helium can of the superconducting magnet and the low temperature cylinder can preferably be thermally anchored at appropriate places in the bore, for example to the helium vapour-cooled shield and the liquid nitrogen-cooled shield or the like. The low temperature cylinder can preferably be connected to the helium can through a capillary at its base. The flow of helium may be controlled by a needle valve regulated from exterior, manually or automatically by computer control means or the like. The flow of helium into the helium bath may be controlled by a motorised needle valve. The level of the liquid can be monitored, e.g. by an Allen Bradley carbon resistor meter, and the needle valve controlled manually or automatically to maintain a fixed level. In order to achieve lower temperatures of the order of 1 K ($^4$He), the bath can be pumped and the temperature of the bath can be ascertained through the helium vapour pressure measured, for example, by an absolute capacitance transducer or Pirani element. If cooled by gas then a temperature measurement can be used to control the needle valve. The cryogen, e.g. helium or nitrogen, could also be supplied from an external reservoir. Closed cycle refrigerators ('cryogen free') could also be envisaged, both for magnet cooling and cooling of the cold space. The sample is polarised by microwave irradiation at the proper frequency. A microwave arrangement is provided for irradiation. The microwave arrangement can be implemented in a number of ways. For lower frequencies (less than ca. 200 GHz) a wave-guide may be used to guide the waves to the sample space. At higher frequencies quasi-optical methods can be employed. The sample space is preferably constructed as a resonant microwave structure. The microwave structure is preferably configured to allow easy placement and exchange of samples and an efficient cooling of samples. Once polarised the sample is dissolved by means of a device and method in accordance with the present invention as described below.

An example of a first embodiment is shown in FIG. 1. The figure shows a cryostat device 1 for polarising a solid material which device 1 is provided with solid polarised material dissolving means in accordance with a first embodiment of the present invention. Device 1 (shown enclosed by dashed lines) comprises a cryostat 2, containing a polarising means 3, e.g. a microwave chamber 3a connected by a wave guide 3b to a microwave source 3c, in a central bore 6 surrounded by magnetic field producing means such as superconducting magnet 5. Cryostats and polarising means for polarising solid material are well known from the prior art and their constructions will not be described in detail. The bore 6 extends vertically down to at least the level of a region P near the superconducting magnet 5 where the magnetic field strength is sufficiently high, e.g. between 1-25 T, for polarisation of the material to take place. The central bore 6 is sealable and can be evacuated to low pressures e.g. pressures of the order of 1 mbar or less. A sample-introducing means such as a removable sample-transporting tube 7 can be contained inside the bore 6 and this tube 7 can be inserted from the top of the bore down to a position inside the microwave chamber 3a in region P. Region P is cooled by liquid helium to a temperature low enough for polarisation to take place, e.g. temperatures of the order of 0.1-100 K. Tube 7 can be sealed at its upper end in any suitable way in order to retain the partial vacuum in the bore 6. A sample-retaining container, such as a sample-retaining cup 9, can be removably fitted inside the lower end of sample-transporting tube 7. This cup 9 is intended to hold any material introduced into tube 7. Cup 9 is preferably made of a light-weight material with a low specific heat capacity such as a foamed plastic, e.g. polystyrene, so that the heat capacity of the cup 9 is as low as possible. A sealable He inlet tube 10 (shown by a dashed line for ease of illustration) extends from the top of bore 6 to the base of cup 9.

The device 1 further comprises means for extracting material from the sample-retaining cup 9. These means for extracting material can comprise an extraction tube 11 that extends from a short distance above the base of sample-retaining cup 9, via a valve 14 to a unit for dissolved polarised material 15. Valve 14 can manually, or preferably, under computer control, be opened to allow communication between extraction tube 11 and the unit for dissolved polarised material 15, and can be closed to prevent such communication. Unit for dissolved polarised material 15 has a hollow body 16 and can be provided with means to speed up the dissolving of solids such as mixing, stirring or agitating means 17 such as an electric knife mixer with blades 19. Preferably all surfaces that polarised material may come into contact with are coated to prevent polarised molecules coming into contact with paramagnetic irons. Unit for dissolved polarised material 15 is preferably surrounded by means for producing a storage magnetic field, such as a permanent magnet 20 or an electromagnet. The expression "storage magnetic field" is intended to mean that the field strength inside the unit for dissolved material 15 should be sufficient to maintain the material hyperpolarised for a period of at least a few seconds and preferably for some minutes. The unit for dissolved polarised material 15 can be at least partly filled with a solvent 21 suitable for dissolving of the material. A source of vacuum V is connectable to the unit for dissolved polarised material 15 via a valve 23 which is preferably computer-controlled by a computer 28. The base of unit for dissolved material contains an outlet 25 that is provided with a valve 27, preferably computer-controlled, for controlling the discharge of the contents of unit for dissolved polarised material 15. The use of computer-controlled, or otherwise automate valves, is preferred as this permits the timing of the opening and closing of the valves to be controlled in an accurate and reproducible manner. Naturally, an operator may be used to initiate a process, for example, by pressing a start button or issuing a start command to a computer.

An example of a method using the first embodiment of the present invention for producing a solution of a dissolved material that has been polarised while in the solid state has the following steps:

the solid material in the form of powder, grains or beads is introduced into the sample-retaining cup 9 at the bottom of the sample-transporting tube 7;

sample-transporting tube 7 is introduced into bore 6 so that sample-retaining cup 9 is positioned in a magnetic field of the necessary field strength, bore 6 is made vacuum tight and evacuated to its working pressure;

the still solid material is hyperpolarised;

unit for dissolved polarised material 15 is partly filled with solvent;

bore 6 is repressurised to atmospheric pressure, where after the upper end of He inlet tube 10 is unsealed;

if the sample-retaining cup 9 is under the surface of the liquid helium in the cryostat then the sample-retaining tube 7 is raised until it is above the surface of the helium;

valve 27 of the outlet 25 is closed and the valve 23 leading to the vacuum supply is opened so that an underpressure occurs in body 16. Valve 23 is closed, valve 14 is opened and the underpressure reigning in body 16 leads to suction forming at the end of extraction tube 11 in the sample-retaining cup 9 and a flow of He from the upper end of He inlet tube 10 through extraction tube 11 to the unit for dissolved material 15. With a suitably high suction, this flow of He gas sucks the hyperpolarised material through tube 11 into the body 16 of the unit for dissolved polarised material 15;

the mixing, stirring and agitating means 17 is actuated while the solid material is sucked into the solvent in order to speed up the dissolving process;

after the material has entered the body 16, valve 23 is closed;

after the material has dissolved the solution of the polarised material can be dispensed through outlet 25 by opening valve 27.

The above embodiment of the invention can be adapted by providing other means for removing the solid hyperpolarised material from the polarising unit. The solid material can for example be ejected from the polarising unit by means of a pulse of pressurised gas (e.g. helium if the sample is in a helium bath). The gas could be introduced into the He inlet tube via a tube from a flask of compressed gas. Or it could conceivably be generated from the bath of liquid helium by supplying a predefined amount of heat to the bath, e.g. by resistive heating, thereby vaporising some of the helium. Or the solid material could be transported from the polarising unit to the unit for dissolved polarised material by mechanical means. For example, instead of extraction tube 11, the sample-transporting tube 7 can contain a movable sample-retaining container, or shuttle, for containing the polarised material. This movable container can be raised or lowered, for example by being connected to a cable or rod, which is connected to an actuating means such as a motor or weight or spring or the like, from the polarising unit to the unit for dissolved polarised material and back again. Once it is in the unit for dissolved polarised material the movable container can tip over, or in some other way deposit the solid material into the solvent. The material container could also be moved by a spring, which is tensioned as the material container is lowered into the polarising unit. When it is desired to extract the container from the polarising unit, the tension in the spring is used to rapidly drag the containing from the polarising unit; or, a loop of high temperature superconductor may be included in the sample holder and a current can be induced in this loop by a surrounding coil. The current can be induced in such a direction that it sets up a magnetic field opposing the main magnetic field, thereby ejecting the sample holder from the sample receiving tube.

In order to limit the loss of polarisation of the dissolved material, the transportation means should be arranged so that the transit time of the polarised material is less than the $T_1$ (spin-lattice) relaxation time of the material while it is being transported from inside the high magnetic field in the cryostat to inside the magnetic field of the unit for dissolved material or other container or apparatus. Preferably this transfer period should be so short that it leads to less than 99% loss of polarisation, more preferably less than 90%, even more preferably less than 10%. The transfer time can be reduced by decreasing the pressure in the unit for dissolved polarised material or adjusting the speed of the mechanical transportation means, etc. During the transferring of the polarised material from the polarising unit, the magnetic field surrounding it will decrease as it moves away from the superconducting magnet. The polarisation of some materials relaxes in low magnetic fields after only a few seconds or much less. In these cases, a strong local magnetic field may be provided by a permanent magnet, superconducting or resistive loop close to the material at least temporarily during the transport. Additionally the transport distances and transfer times should preferably be made as short as possible. In order to achieve the best results, the polarising unit and the unit for dissolved polarised material should preferably be placed in a strong magnetic field, e.g. of the order of 0.1-25 T. As is obvious to the skilled person the actual magnetic field strength required in any case will vary with the type of solid and dissolving method used. For some molecules the relaxation in solution is temperature dependent and an optimal temperature of the solution can be chosen to preserve the polarisation for as long as possible. In general, but not always, the magnetic field should be as strong as possible during the dissolving. The minimum $T_1$ during the process of dissolving will generally increase with increasing magnetic field. Furthermore, the relaxation time will depend on the magnetic field and an appropriate magnetic field can be applied during transport of the solution (for example during transport of the solution from the polarising means to the imaging magnet).

In order to keep the solid hyperpolarised material as cold as possible during its transportation to the unit for dissolved polarised material, it is preferable to use materials which have a low thermal conductivity and low specific heat capacity for the tubes, e.g. Teflon™, polyurethane, silicon or the like. Additionally the tubes could be made double walled and/or silvered in order to reduce heat transfer by conduction and/or radiation.

Figure 2:
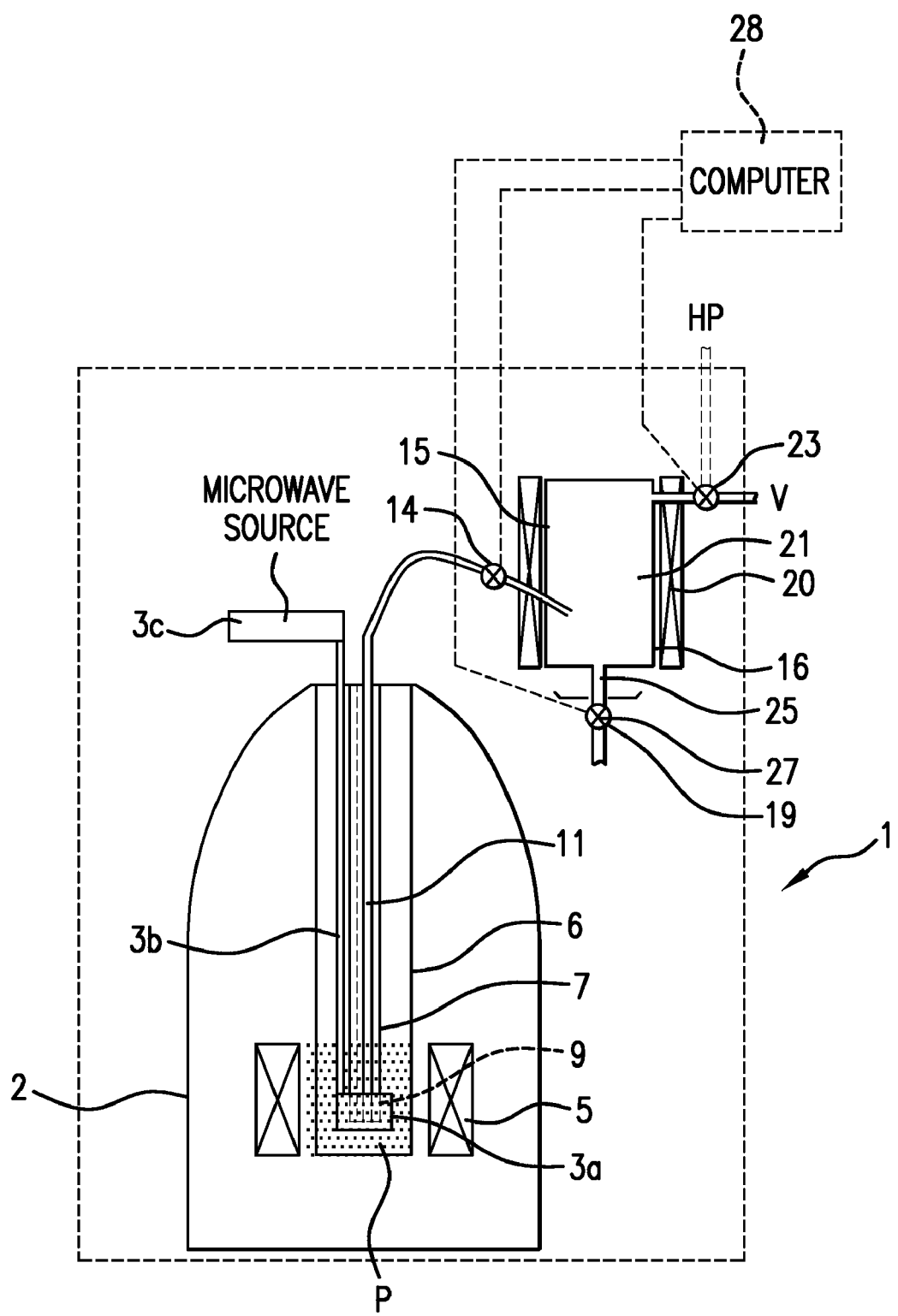
FIG. 2 shows a schematic lateral view of a second embodiment of a device in accordance with the present invention.

In a second embodiment of the present invention, illustrated schematically in FIG. 2, dissolving of the hyperpolarised material in the sample-retaining cup 9 can be performed while the material is still inside the cryostat device 1. This can be achieved by providing a solvent introducing means. This can, for example, be achieved by supplying a suitable high-pressure gas or fluid HP, e.g. air or helium or solvent, to valve 23 as shown by dotted lines in FIG. 2.

An example of a method using the second embodiment of the present invention for producing a solution of a solid material that has been polarised while in the solid state has the following steps:

the solid material in the form of powder, grains or beads is introduced into the sample-retaining cup 9 at bottom of the sample-transporting tube 7;

sample-transporting tube 7 is introduced into bore 6 so that sample-retaining cup 9 is positioned in a magnetic field of the necessary field strength, bore 6 is made vacuum tight and evacuated to its working pressure;

the still solid material is hyperpolarised;

unit for dissolved material 15 is partly filled with solvent;

bore 6 is repressurised to atmospheric pressure and the upper end of He inlet tube 10 is unsealed;

if the sample-retaining cup 9 is under the surface of the liquid helium in the cryostat then the sample-transporting tube 7 is raised until it is above the surface of the helium;

valve 27 of the outlet 25 is closed and the valve 23 is adjusted so that it connects the body 16 to the high pressure gas or liquid supply HP so that an overpressure occurs in body 16. Valve 14 is opened. This leads to solvent from body 16 being forced into the sample-transporting tube 7. Once a volume of solvent sufficient or more than sufficient to dissolve the solid material has been delivered to the sample-transporting tube 7, valve 23 is closed. The solvent in the sample-transporting tube 7 comes into contact with and dissolves the hyperpolarised solid material in the sample-retaining cup. Optional mixing, stirring or agitating means (not shown) acting on the material in the sample-retaining cup 9 can be provided in order to speed up the dissolving of the material.

If it is desired to then extract the solution of dissolved hyperpolarised material from the cryostat (instead of analysing it in situ) then the valve 23 leading to the vacuum supply is opened so that an underpressure occurs in body 16. This leads to suction forming at the end of tube 11 in the sample-transporting tube 7 and a flow of He from the He inlet tube 10 through tube 11 to the unit for dissolved material 15. This flow of He sucks the solution of hyperpolarised material through tube 11 into the body 16 of the unit for dissolved polarised material 15;

after the material and solvent have entered body 16, valve 23 is closed;

a mixing, stirring and agitating means 17 in the unit for dissolved material is optional in this embodiment, but if it is provided then it can be actuated for a predetermined period of time in order to ensure that the solid material is fully dissolved;

the solution of the hyperpolarised material can then be dispensed through outlet 25 by opening valve 27.

Preferably this method is automated, for example by being controlled by computer (not shown), and computer-controlled actuators (not shown) are provided to operate valves and mixing, stirring or agitating means.

In a further embodiment of the present invention a solvent can be added to the sample-retaining cup 9 by simply injecting the solvent into the open upper end of sample-transporting tube 7. The solution of solvent and dissolved polarised material can then be aspirated in any suitable manner, or the solution can be ejected through an outlet by injecting more solvent or a gas or the like.

When the polarised solid material is brought into solution phase inside the polarising unit by introducing the solvent into the polarising unit as in the second embodiment of the present invention, the polarised solid material is dissolved while kept in the strong magnetic field of the polarising unit or close to the strong magnetic field area of the magnet. If the material is polarised in a helium (or nitrogen) bath, the material can be raised from the bath to drain the liquid coolant prior to dissolving. The sample would still experience a significant part of the magnetic field of the polarising unit. The solvent can then be introduced into the sample retaining cup and mixed with the solid material to rapidly dissolve the solid after which the solution could be extracted with a syringe (either manually or automatically) or by a flow system as described above and injected into the item being imaged or simply directly analysed by solution NMR.

Several factors have to be taken into account when the polarised solid material is brought into solution phase inside the polarising unit. As mentioned above, one factor is heat loss of the liquid entering the polarisation unit, as it is important that it does not freeze when it comes into contact with the cold sample-retaining container and solid material. Therefore the amount of solvent added should have a mass and specific heat capacity such that it has enough thermal energy to prevent it from freezing when it is dissolving the solid material. Water is a good choice of solvent due to its high specific heat capacity and high latent energy of solidification. It is also the solvent of choice for biological reasons when the sample is to be used in vivo. Other suitable solvents are biological buffers such as Ringer's acetate. When the sample is to be analysed by NMR spectroscopy or analytical high resolution NMR spectroscopy, a wider range of solvents is possible and it is especially advantageous to use water with anti-freeze additives such as glycerol. Another important factor is the design of the tubing to introduce the solvent and the design of the sample-retaining container. Lightweight materials with poor thermal conductivity and a low specific heat capacity are preferred so that the heat energy lost by the solvent to the tubing when descending into the bore and the energy lost to the sample-retaining container are kept to a minimum. Typical suitable materials are Teflon™, polyurethane, PEEK, Aerogel™ and Perlite™. It can also be useful to use double wall tubing (the inner tube might be inserted immediately prior to solvent addition). It can additionally be advantageous to evacuate the space between the walls of double wall tubes. Tubes can also be silvered or coated with an insulating film (for example aluminised Mylar™). It can also be advantageous to include a wrapping of resistive heating wire or film on the tubing to improve the means of controlling the temperature of the sample. Another factor to take into account is the material used for manufacturing the sample-transporting tube and any sample holder used. The same criteria for choice of material as above applies here but ceramic materials can be especially suitable here. For example, it can be useful to use a ceramic or foamy plastic material that is porous to the extent that superfluid helium easily can circulate through the walls of the sample receiving tube and/or sample holder to cool the solid material while liquid water or other solvents cannot circulate through the walls. This allows the material to be cooled by immersing the sample-retaining container in the form of a cup or closed end tube in a liquid helium bath, then lifting the container above the surface of the liquid helium so that liquid helium drains out through the pores of the container before adding the water. Subsequent to the dissolving of the sample, the sample has, in the case of in vivo applications, to be extracted from the sample holder. This can be done either by the methods in accordance with the present invention described above e.g. by a flow system, where liquid is pumped through the sample holder, by suction or by pressurising the sample container and collecting the polarised solution outside the polarising unit in a unit for dissolved polarised material, for example in a syringe so that it is ready for injection in to the subject.

Figure 3:
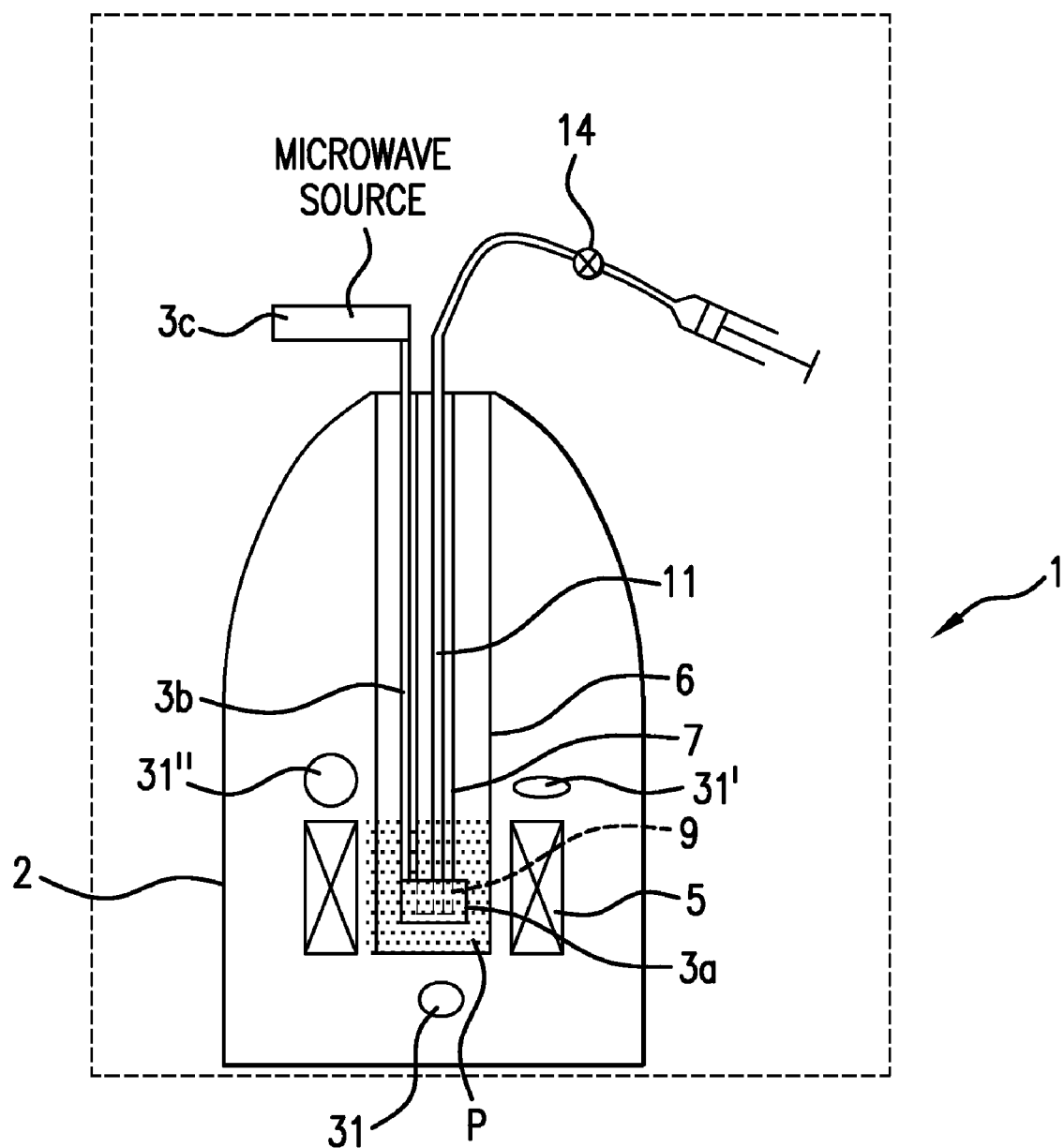
FIG. 3 shows a schematic lateral view of a third embodiment of a device in accordance with the present invention; and, FIG. 4 shows schematically a section through a device for injecting hot solvent in accordance with the present invention.

In a third embodiment it is also conceivable to provide the analytical NMR instrument in the same instrument as the polarising unit and dissolving unit. This is shown in FIG. 3, where there is a plurality of analysis coils 3*l*-3*l*''', i.e. nuclear magnetic resonance imaging coils and/or nuclear magnetic resonance spectroscopy coils. Coils which can be used for field shimming and NMR signal acquisition can be placed in positions that are known from high resolution analytical NMR. In this case, the unit for dissolved polarised material is the same as the sample-retainer cup, and the transport time is zero seconds. This is advantageous, as in this case there is no need to move the sample out of the magnetic field of the superconducting magnet when performing the analysis i.e. imaging or spectroscopy. Additionally, the low operating temperature of the coils immersed in liquid helium improves their signal to noise ratio by a significant factor (of more than 3). The requirements concerning field strength may not be identical for the polarisation and the NMR detection, and means may be provided for moving a sample from one part of the magnet to another. The NMR detection could advantageously be done at a lower or higher field than optimal for the DNP process. One implementation would therefore be that the DNP polarisation is done in cold helium gas at the lower edge of the magnet (i.e. in a lower field, e.g. 3.35 T). The field would then have to be shimmed in this area to the required homogeneity. After the polarisation the sample could then be lifted to the magnet centre (that has a higher field, e.g. 9.4 T, and homogeneity) for dissolving and NMR detection. Furthermore, the sample could be lifted to an intermediate place for dissolving and then moved to the magnet centre for NMR detection.

A conceivable variation of the invention is the incorporation of a multiple sample holder into the device so that several samples can be polarised at once or sequentially and either ejected or dissolved one by one. It is also conceivable to use a system where several samples are dissolved and analysed simultaneously. As is obvious to the skilled person, a multiple sample holder system can be fashioned in many different ways e.g. using a carousel type holder or a grid-type holder.

In a fourth embodiment it is possible to provide prior art NMR equipment with a device in accordance with the present invention in order to produce an apparatus that can produce materials with a high polarisation by DNP. In order to do this the NMR equipment needs be provided with a low temperature space that is in a magnetic field. In order to achieve this, any ordinary NMR magnet that has a suitably wide bore size may be equipped with a flow cryostat and instrumentation as described below in order to enabling the production of solutions of molecules with DNP enhanced nuclear polarisation. A flow cryostat is a vacuum insulated chamber that may be inserted into the bore of a magnet normally designed to have a room temperature bore, thereby allowing the temperature of the bore to be lowered by a stream of a cold cryogen. The flow cryostat is usually connected to an external cryogen supply through a transfer line and the flow of cryogen into the flow cryostat cools the bore of the magnet and forms a low temperature space. The flow cryostat may be equipped with means, described below, to enable the polarisation of solid materials by DNP and it may be equipped with instrumentation, described below, for the detection of nuclear signals in the solid state and in solution. Note that in dedicated DNP systems for NMR analysis or production of hyperpolarised imaging agents the low temperature space is preferably integrated into the magnet cryostat.

Figure 6:
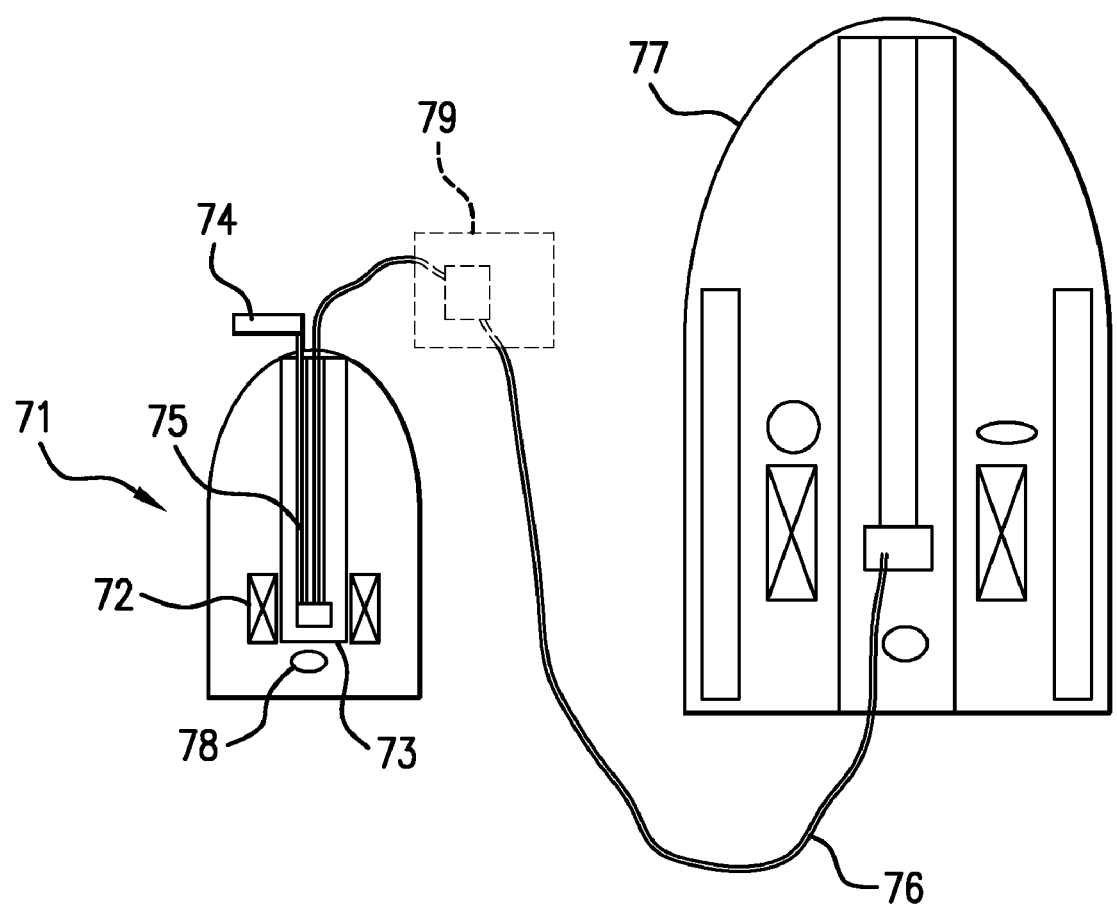
FIG. 6 shows schematically a lateral view of a device, for producing hypexpolarised materials by DNP, interfaced to a NMR spectrometer; and, FIG. 7 shows schematically an embodiment of a magnetic resonance measurement circuit.

The embodiment described above discloses a DNP device, which performs the present invention in an in situ approach (i.e. the polarisation, dissolving and NMR detection are both performed in the same instrument). It has the disadvantage that existing NMR spectrometers cannot easily be reconfigured for DNP enhanced spectroscopy. In order to overcome this, a further embodiment of the present invention will now be described and illustrated in FIG. 6 in which a DNP device 71 comprising a magnetic field-generating unit 72, e.g. superconducting magnet, permanent magnet or electromagnet, provided with an internal cold space 73 where a sample can be positioned and where a microwave-generating unit, for example, consisting of a microwave source 74 and a wave guide arrangement 75, can be present in order to polarise the sample, is arranged in proximity to and connectable by a polarised material transfer line 76 to a NMR spectrometer 77. Further NMR coils 78 may optionally be present in the DNP unit in order to quantify the magnetisation of the sample in the solid state and/or in solution). The polarised sample can be extracted from the cold space as a solid and dissolved in a unit for polarised material 79 (shown by dashed lines between the DNP unit 71 and the NMR spectrometer 77) or it can be dissolved in situ as described above. Some flexibility exists in the positioning of the DNP apparatus relative to the NMR magnet. However as short a distance as possible is preferred in order to reduce the transit time of the dissolved polarised material between the DNP device and the NMR spectrometer. The advantage of this configuration is that it can be provided as an upgrade for existing NMR spectrometers. The reconfiguration of the NMR spectrometer for DNP hyperpolarisation is quick and easy. Existing NMR probes (flow probes) can be easily interfaced and full advantage from current NMR technology can be taken. The polarised liquid sample should leave the DNP apparatus as quickly as possible and be positioned in the flow probe active region for immediate NMR analysis and therefore accurate timing of the entire polarisation, dissolving, transporting process and triggering of the NMR excitation/acquisition once the sample is in the NMR spectrometer is required. This may conveniently be computer controlled in order to ensure that the transit time for the liquid and the delay between its arrival in the NMR spectrometer and the triggering of the NMR excitation/acquisition is preferably shorter than the nuclear $T_1$.

Figure 4:
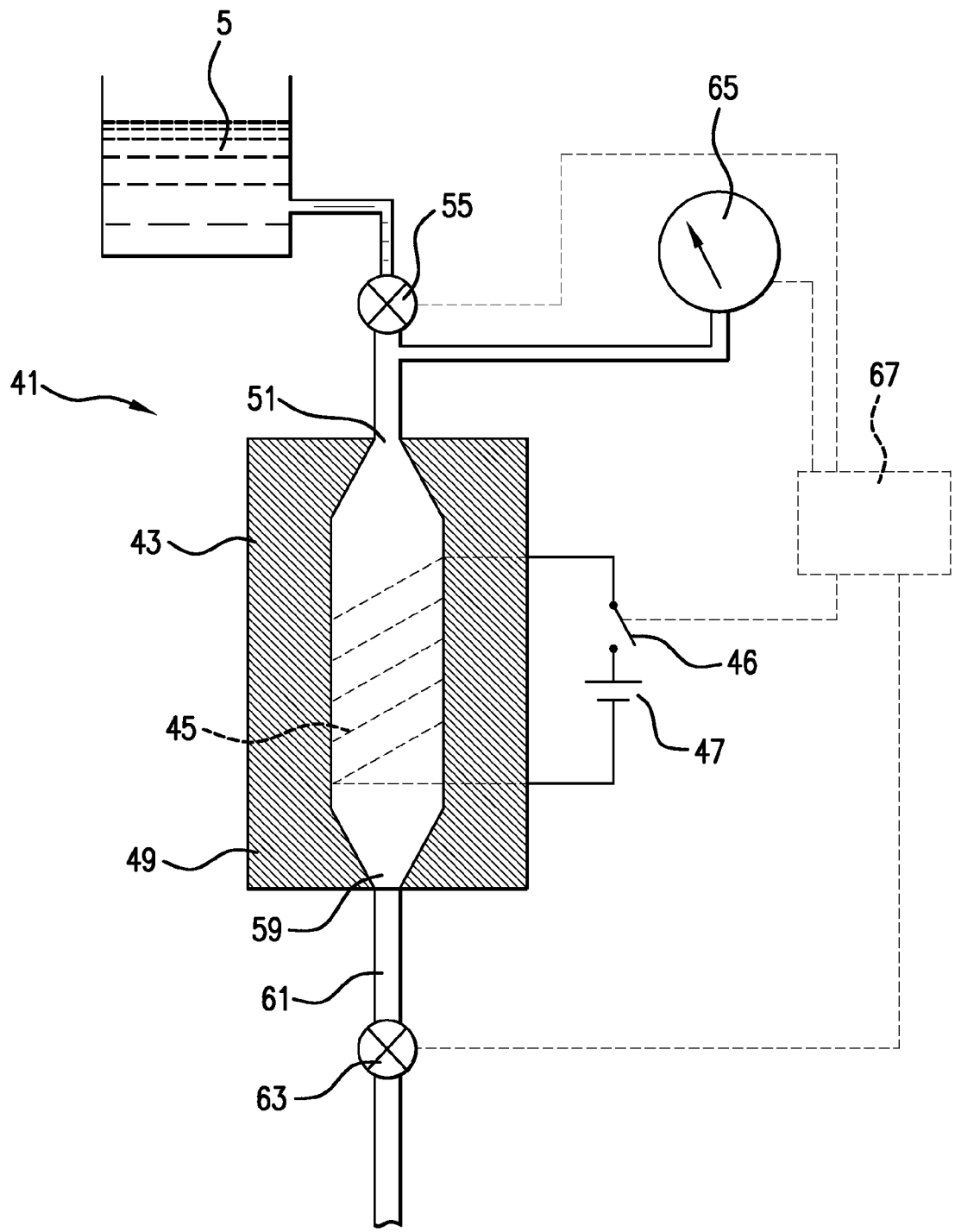

FIG. 4 shows schematically a cross-section through an embodiment of a solvent heating and injecting device 41 suitable for injecting heated solvent into a sample-retaining container, e.g. a sample-retaining cup in a cryostat. Solvent heating and injecting device 41 comprises a pressure container 43, capable of resisting pressures of at least 2 bar, and preferably 10 bar, which pressure container 43 can be heated by heating means such as heating coil 45 wrapped around pressure container 43 and connectable via a switch or relay 46 to a power supply 47. Pressure container 43 is preferably thermally insulated, for example by an insulating jacket 49 that surrounds it. Pressure container 43 is provided with an inlet 51, connectable via an inlet pipe 53 and inlet valve 55 to a supply of solvent 57, and an outlet 59 connectable via an outlet pipe 61 and outlet valve 63 to a sample-retaining container (not shown). A pressure sensing device such as a pressure transducer 65 is connectable to solvent heating and injecting device 41 in order to measure, and optionally display, the pressure in pressure container 43. The solvent heating and injecting device 41 works in the following way: with outlet valve 63 closed, inlet valve 55 is opened to
  permit a quantity of solvent sufficient to dissolve the polarised sample to enter pressure container 43 and then valve 55 is closed;
switch 46 is closed so that heating coil 45 is connected to power supply 47 and the solvent in pressure container 43 is heated;
the rise in temperature causes the solvent to begin boiling and this causes the pressure inside the pressure container 43 to rise;
when the pressure registered by pressure transducer 65 has reached a predetermined value, e.g. 2 bar or 5 bar, which corresponds to the temperature needed to dissolve the sample, power supply 47 is disconnected, outlet valve 63 is opened and the excess pressure over ambient pressure which is present in the pressure container 43 causes the solvent to be rapidly ejected via outlet pipe 61 to the sample-retaining container where it dissolves the sample.

As shown by dashed lines, preferably valves 55 and 63, pressure transducer 65 and heating coil 45 are connected to a control means such as computer 67. Computer 67 is preferably provided with software for controlling solvent heating and injecting device 41 and, if applicable, for controlling means for removing the dissolved polarised sample from the sample-retaining container.

Figure 5:
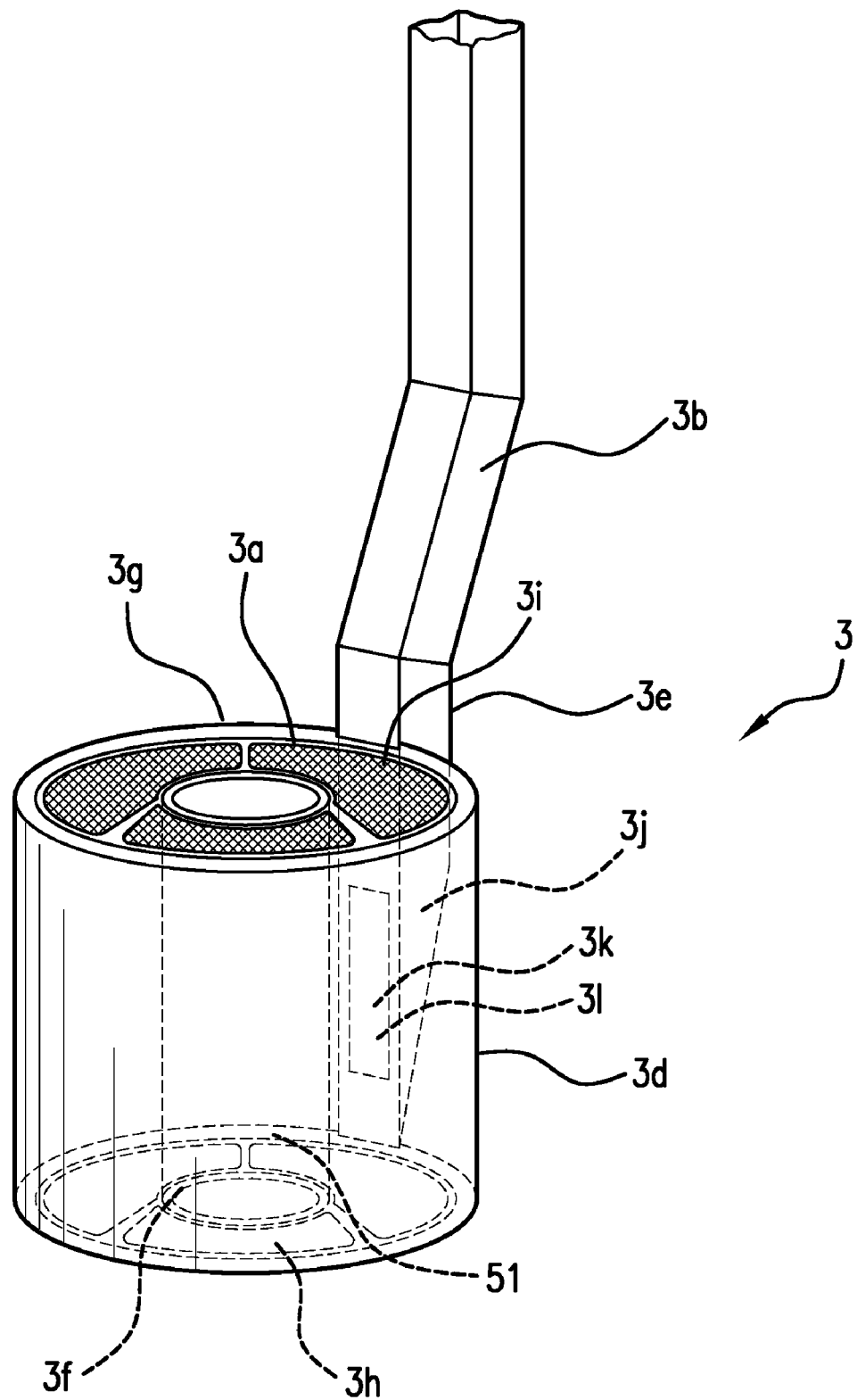
FIG. 5 shows an embodiment of a sample-retaining container in accordance with the present invention.

A sample holder and a suitable microwave structure may be placed in the cold space in order to achieve microwave irradiation of the sample. The microwave structure can be a horn antenna or a chamber attached to the end of a wave-guide (as shown in FIG. 5) or a set of Fabry-Perot mirrors or any other suitable microwave irradiating structures. The microwave structure is preferably designed to act as a resonance chamber for microwaves in order to increase the strength of the microwave field in the microwave structure. For the lower frequencies (less than ca. 200 GHz) wave-guides may conveniently be used to guide the waves to the irradiating structure. The geometry and dimensions of the wave-guide are chosen in order to reduce microwave losses. Preferably the wave-guide is designed to have as low a heat load to the low temperature space as possible, and can be made, for example, from silver plated thin-walled stainless steel. Corrugated wave-guides could also be used. At higher frequencies quasi-optical methods can be employed, and the microwave can be guided with lenses and mirrors. The microwave structure preferably has openings to allow an easy exchange of sample and efficient cooling of the sample. A suitable microwave oscillator generates the microwaves, e.g. an IMPATT diode oscillator, or an IMPATT amplified Gunn oscillator, or a BWO or the like. Furthermore, the microwave oscillator may be an integrated part of the resonant structure for irradiating the sample. Thus the active device producing the microwaves may be physically placed in the magnet close to the sample whereby transmission losses would be reduced.

FIG. 5 shows a perspective view of part of an embodiment of a polarising means 3 intended to be placed inside the cryostat of a DNP system. This comprises a microwave chamber 3a connected by a wave-guide 3b to a source of microwave energy (not shown). Chamber 3a has a substantially cylindrical outer wall 3d, an upper end plate 3e and a lower end plate 3f.

Chamber 3a is made of a microwave reflecting material such as brass. Upper end plate 3e has a central circular opening 3g with a diameter adapted to allow a sample-retaining cup 9 (not shown) to pass into the chamber 3a. Upper and lower end plates 3e, 3f have a plurality of cutouts 3h which are covered by a microwave reflecting mesh 3i which allows liquid helium to enter the chamber 3a while preventing microwaves from leaving the chamber 3a through the cut-outs 3h. The chamber 3a is mounted on the lower end 3j of the wave-guide 3b and a slot 3k in the wall 3d of the chamber 3a is aligned with a similar slot 3l in the lower end 3j of the wave-guide 3b in order to allow microwaves to pass from the wave guide 3b into the chamber 3a. The dimensions of the slots 3k, 3l are adapted to optimise the flow of microwaves into the chamber 3a. For example, if the inner diameter of the chamber is 28 mm, the inner height is 28 mm and the internal width of the wave-guide is 7 mm, then the slots can be 5-10 mm high and 2-7 mm wide. The lower end 3j of the wave-guide 3b is tapered towards the bottom in order to act as a microwave reflector for increasing the amount of microwave energy coupled into the chamber 3a. Suitable angles of taper depend on the dimensions of the wave-guide, the microwave frequency used and the dimensions of the slots 3l, 3l, but can be from about 5° to 60°, but preferably from 15° to 30°. The dimensions of the chamber 3a, wave-guide 3b, slots 3k, 3l are adapted so that chamber 3a acts as a resonance chamber for the microwave energy. In order to measure the polarisation of a sample contained in a sample-retaining cup, the chamber can be optionally provided with a central NMR pick-up coil 51. This can be suitably made of a cylinder 53 made of PTFE provided with, depending on the static field orientation, helical or saddle shaped copper windings (not shown) and connected to suitable sensing means.

In this embodiment, a sample is placed in a sample-retaining cup 9 and the sample retaining container is lowered into the centre of the chamber 3a (inside the pickup coil if there is a pick up coil). The source of microwave radiation is activated and the sample irradiated. It can then be dissolved by means of the methods described above (i.e. in situ in the cryostat or in a unit for dissolve polarised material outside the cryostat) and the dissolved polarised sample held in the unit for dissolved polarised material, or some other container (e.g. the sample retaining cup) in a strong magnetic field, until needed.

In a second embodiment of a chamber in accordance with the present invention, the lower end plate 3f has a central hole 3m of the same diameter as a sample-retaining cup 9. This allows the sample-retaining cup 9 to be lowered through the chamber 3a and out the bottom of it. A sample-receiving container could be provided with a plurality of vertically separated sample-retaining cups. These cups could each be the height of the chamber 3a or a fraction thereof. If they are the same height as the chamber 3a then it would be possible to expose a first sample in one cup to microwaves in the chamber 3a while a second sample in a second cup is positioned outside the chamber, but still very close to the strong magnetic field. When the first sample is sufficiently polarised the sample receiving container can be moved vertically so that the second sample in the second cup is inside the chamber 3a and the polarised first sample in the first cup is maintained polarised in the magnetic field outside the chamber 3a. This can be repeated until all the samples have been polarised, then all the samples can be dissolved at once, using one device, or a plurality of devices, for extracting material from the sample-transporting tube. Alternatively, each polarised sample could be dissolved in turn and either stored in the liquid phase in its cup (which is therefore a unit for dissolved polarised material) in the strong magnetic field in the DNP unit or in another unit for dissolved polarised material in the magnetic field of an imaging or spectrometry device.

NMR detection is particular desirable for analytical applications. For other applications NMR detection optionally provides a measure of the nuclear polarisation. The NMR detection coil could be of any known design, e.g. solenoid or saddle shaped. Usually the coil (inductance) is tuned to the NMR frequency with a capacitor and matched to the characteristic impedance of the cabling. The NMR coil could be tuned and matched at a number of frequencies in order to detect the nuclei of interest. The capacitors could be mounted close to the coil in the cold space. This would allow the highest Q-values to be obtained. In the event that it is impractical to have the capacitors close to the coil, then they may be put outside the cold space and connected to the low temperature space via a transmission line. The transmission line could be coaxial, twisted pair, stripline, or any other suitable cabling. The choice will be a compromise between heat load to the cold space and signal attenuation. Several coils could also be envisaged. They could be tuned for two NMR frequencies and would allow double resonance NMR (decoupling, cross polarisation, etc) to be performed in both solid state and liquid phase. This would also allow simultaneous detection of nuclei of more than one nuclear species. The spectrometer would then have to have multiple receivers. Optionally, the NMR signal of the various nuclei could be acquired sequentially. In order to permit multiple samples to be analysed in a short space of time, a sample-carousal for moving samples may be provided. Additionally, the dissolving of the solid material may be detected by optical means, as in order to perform reproducible NMR analysis it is important that the material to be examined is dissolved homogeneously. This may be checked by using optional optical photo-detection means inside or outside the NMR analytical chamber. Since some of the nuclei of interest may have very short $T_1$ values it can be important to secure analysis as soon as the dissolving process is finished. It is therefore preferable to have means arranged for coincident excitation/detection of all nuclei of interest. If the NMR detection circuit is cooled then a better signal-to-noise ratio is obtained. Furthermore, cooling of the signal amplifier is often advantageous. Consequently the signal amplifier may be positioned close to the NMR detection circuit and preferably in the cold space. Superconducting coils and SQUID detectors are other devices that are available to improve the signal-to-noise ratio.

Figure 7:
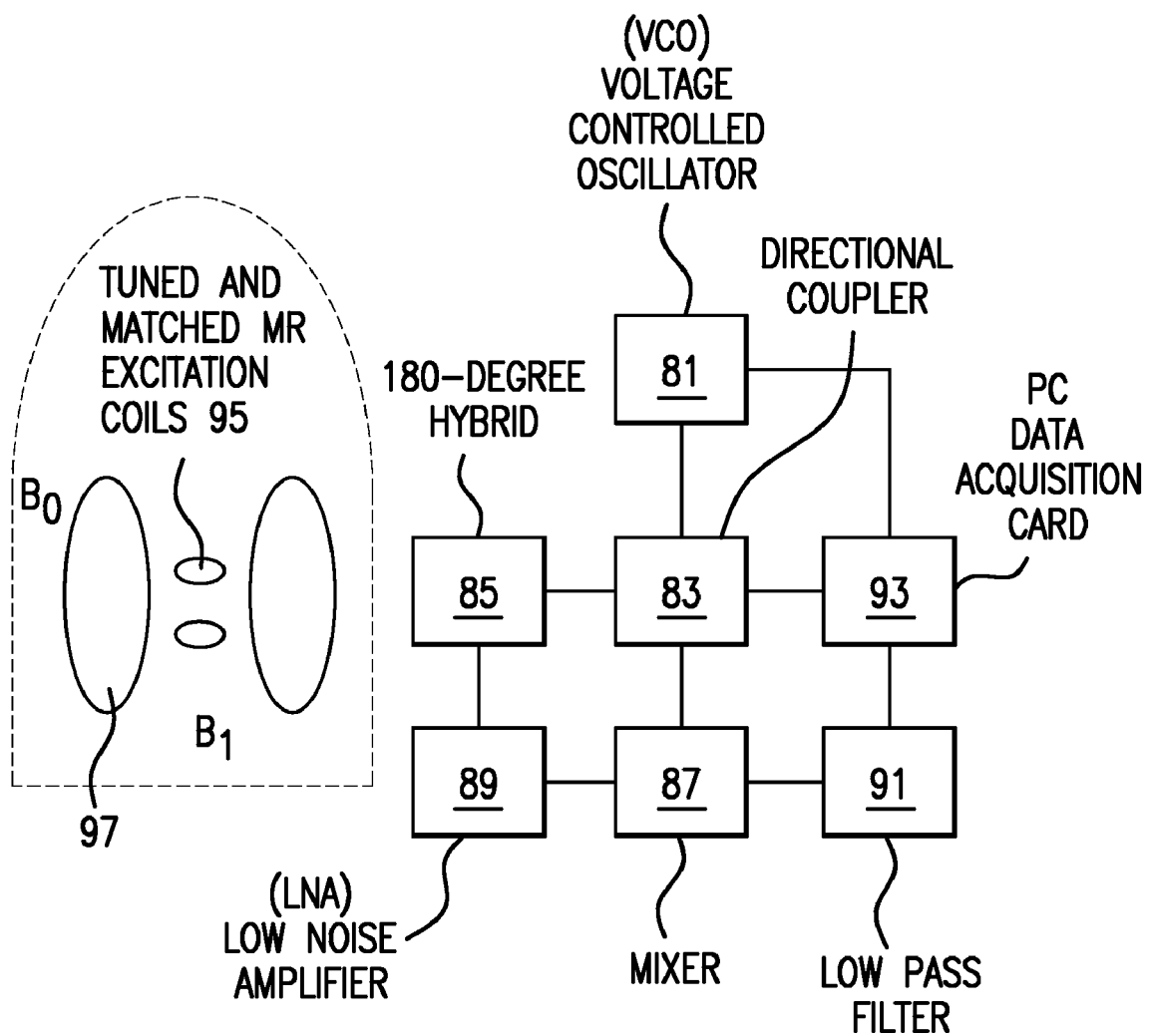

A simple and cheap circuitry that can be used for simple polarisation measurements is shown in FIG. 7. The device is a simple radio frequency magnetic resonance spectrometer. Such a device can be used to determine the polarisation of the solid sample material before it is dissolved and uses any of the previous described detection coils. The RF circuit consists of a VCO (voltage controlled oscillator) 81, a directional coupler 83, a 180-degree hybrid 85, a mixer 87, a LNA (low noise amplifier) 89, a low pass filter 91, a PC data acquisition card 93, and tuned and matched MR (or excitation) coils 95 (giving magnetic field $B_1$) arranged to provide a nearly uniform field transverse to the direction of the static field $B_0$ from static field coils 97. The coils 95 are tuned to the MR frequency and matched to the characteristic impedance of the transmission line (e.g. 50 Ω). The VCO 81 (or function generator) generates a continuous wave signal that is split by directional coupler 83 (divider) into two signals, which drives the local oscillator of the mixer 87 and the other to 180-degree hybrid 85 feeding the MR coil 95. Fixed attenuators (not shown) may be used to adjust the signal levels. The VCO 81 should be capable of being frequency modulated over a sufficient frequency range to cover the spectra range of interest. The modulation rate could be typically 5-50 Hz, and the modulation signal is supplied synchronously with the signal acquisition (signal averaging). Preferably the modulation-signal and signal acquisition is generated from a PC data acquisition card 93, and the signal is conveniently available for further data analysis. A change of reflection coefficient is observed as the frequency is swept through the magnetic resonance. The reflection signal is amplified by the LNA 89 and fed to the mixer 87. By adjusting cable lengths an absorption or dispersion signal can be chosen. The bandwidth of the MR coils 95 in itself produces a parabolic baseline, which has to be subtracted from the signal. The baseline can be acquired before introducing the sample or it can be fitted with a polynomial function (or a spline function) outside the signal regions. The coil bandwidth can be adjusted for optimal performance in a number of ways, e.g. resistive damping, overcoupling which gives a better result, or, preferably, by actively loading the coils 95 with the LNA 89. The natural bandwidth of a tuned coil in this frequency regime is several hundred Hz, providing insufficient bandwidth for most applications. Resistive damping increases the useful bandwidth to an acceptable degree. However, this compromises the signal-to-noise ratio by the square root of the increase. This is acceptable to some extent since amplitude and phase-noise of the VCO often determine the signal-to-noise ratio. The magnetic field could be anything from a few mT to many T depending on the gyromagnetic ratio of the spin and the frequency of the VCO 81.

As is clear to the skilled person, in a method in accordance with the present invention the presence of a strong magnetic field, and, optionally, elevated/optimised solvent temperature, agitation, and a finely divided solid sample minimises the polarisation loss during dissolving. The amount of polarisation retained during the dissolving of any particular solid polarised material depends on, amongst others, the following factors: the composition of the polarised material, the form and size of the material (e.g. whether it is in the form of beads, powder, particles, or is present as a solid mass) the solvent used to dissolve it, the solvent temperature, the speed of dissolving, the magnetic field the dissolving takes place in. By optimising these factors for each material, loss of polarisation can be made negligible. The optimum conditions for the dissolving a sample while retaining a high level of polaraisation can be readily found experimentally The following experimental results show the results of varying the time taken to dissolve a sample, all other variables remaining the same: dissolving 1 mm diameter beads of HP001 (1-hydroxymethyl-1-13C-cyclopropyl)-methanol, doped with 15 mM OX063, in $D_2O$ at a temperature of 360K in a time of 3 s in a magnetic field of 3.35 T resulted in a loss of polarisation of less than 10%. Dissolving the same substance in 8 s resulted in a loss of polarisation of 69%. Performing dissolving of the same substance in 12 s caused a loss of polarisation of 97%. These results were reproducible and allow the degree of polarisation lost during dissolving at different rates to be estimated. Thus, these results show that dissolving HP001 in 12 seconds leads to a loss of polarisation of less than 99% (actually 97%), dissolving HP001 in 8 seconds leads to a loss of polarisation of less than 90% (actually only 69%) and dissolving HP001 in 3 s causes a loss of polarisation of less than 10%. More rapid dissolving, for example achieved by more agitation or a higher solvent temperature leads to even smaller losses in polarisation between the solid and liquid states.

The above mentioned embodiments are intended to illustrate the present invention and are not intended to limit the scope of protection claimed by the following claims.

The invention claimed is:

1. A device configured for polarising a solid material and dissolving such a solid polarised material in a solvent wherein said device comprises a cryostat (2) configured to receive a sample-retaining container and configured for retaining a sample of the solid material and comprising magnetic field generating means (5) and means (3a-3c) for polarising the solid material, wherein said device further comprises means for dissolving the solid polarised material (14, 15) in said solvent in said sample-retaining container (9) while said sample-retaining container is inside said cryostat (2).

2. A device in accordance with claim 1, further comprising means for extracting and transporting said polarised material, said means for extracting and transporting said polarised material being configured to transport said polarised material in solution from said sample-retaining container (9) inside said cryostat to a unit for dissolved polarised material (15) arranged outside said cryostat.

3. A device in accordance with claim 2, wherein said means for extracting and transporting said polarised material is further configured to transport solvent to said sample-retaining container (9) positionable inside said cryostat.

4. A device in accordance with claim 1, wherein the loss of polarisation during dissolving of said polarised solid material is less than 99%.

5. A device in accordance with claim 1, wherein the loss of polarisation during dissolving of said polarised solid material is less than 90%.

6. A device in accordance with claim 1, wherein the loss of polarisation during dissolving of said polarised solid material is less than 10%.

7. A device in accordance with claim 2, wherein said unit for dissolved polarised material (15) is provided with agitating, stirring or mixing means (17, 19).

8. A device in accordance with claim 1, wherein said device further comprises a dynamic nuclear polarisation system.

9. A device for nuclear magnetic resonance analysis comprising the device of claim 1 and nuclear magnetic resonance analysis coils (31-31").

10. A method for producing a solution containing a dissolved polarised material, said method comprising the steps of:

introducing into a cryostat (2) of a device according to claim 1 a solid material in a sample-retaining container (9);

polarising said solid material inside said cryostat (2) of said device; and dissolving said polarised material in said sample-retaining container (9) in a solvent while still inside of said cryostat (2) of said device.

11. A method in accordance with claim 10, wherein the loss of polarisation of said polarised solid material during said dissolving step is less than 99%.

12. A method in accordance with claim 10, wherein the loss of polarisation of said polarised solid material during said dissolving step is less than 90%.

13. A method in accordance with claim 10, wherein the loss of polarisation of said polarised solid material during said dissolving step is less than 10%.

14. A device in accordance with claim 1 wherein the sample-retaining container (9) is a multiple sample holder and several samples of the solid material can be polarised at once or sequentially.

15. A method in accordance with claim 10 wherein the sample-retaining container (9) is a multiple sample holder and several samples of the solid material can be polarised at once or sequentially and wherein said several polarised samples are dissolved one by one or simultaneously.

16. A method in accordance with claim 10 wherein subsequently NMR analysis of the dissolved polarised material is performed.

* * * * *